US009410930B2

(12) United States Patent
Decitre

(10) Patent No.: US 9,410,930 B2
(45) Date of Patent: Aug. 9, 2016

(54) METHOD FOR MANUFACTURING A TESTING HEAD OF A NON-DESTRUCTIVE TESTING SENSOR BASED ON EDDY CURRENTS

(71) Applicant: Commissariat a l'energie atomique et aux ene alt, Paris (FR)

(72) Inventor: Jean-Marc Decitre, Marcoussis (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 240 days.

(21) Appl. No.: 14/365,824

(22) PCT Filed: Dec. 4, 2012

(86) PCT No.: PCT/FR2012/052797
§ 371 (c)(1),
(2) Date: Jun. 16, 2014

(87) PCT Pub. No.: WO2013/093278
PCT Pub. Date: Jun. 27, 2013

(65) Prior Publication Data
US 2014/0352136 A1 Dec. 4, 2014

(30) Foreign Application Priority Data

Dec. 22, 2011 (FR) ...................................... 11 62342

(51) Int. Cl.
*H01F 7/06* (2006.01)
*G01N 27/90* (2006.01)

(52) U.S. Cl.
CPC .......... *G01N 27/9033* (2013.01); *G01N 27/904* (2013.01); *Y10T 29/4902* (2015.01)

(58) Field of Classification Search
CPC .......... G01L 1/14; G01L 1/127; G01N 27/82; G01N 27/9046; G01N 25/72; G01N 27/023; G01N 27/72; Y10T 29/49007; Y10T 29/4902
USPC ...................... 29/602.1, 595, 603.01, 603.09; 324/237, 238, 240, 241, 242
See application file for complete search history.

(56) References Cited

U.S. PATENT DOCUMENTS 4,677,379 A * 6/1987 Arnaud .............. G01N 27/9046
324/240
6,310,476 B1 10/2001 Kawanami et al.
(Continued)

FOREIGN PATENT DOCUMENTS

EP 2 056 103 5/2009
FR 2 881 826 8/2006
(Continued)

OTHER PUBLICATIONS

Avrin, W. F. "Eddy current measurements with magneto-resistive sensors: Third-layer flaw detection in a wing-splice structure 25 mm thick" Nondestructive Evaluation of Aging Aircraft, Airports and Aerospace Hardware IV, Proceedings of SPIE, vol. 3994, pp. 29-36, 2000 (XP 055032845).
(Continued)

*Primary Examiner* — Thiem Phan
(74) *Attorney, Agent, or Firm* — Oblon, McClelland, Maier & Neustadt, L.L.P.

(57) ABSTRACT

A method for manufacturing a testing head of a non-destructive testing sensor based on eddy currents includes: optimizing a geometric design of coils of the testing head based on a criterion for minimizing an electromotive force induced in at least one coil having a receiving function and/or maximizing a variation, due to presence of a standard defect to be detected in a part to be inspected, of the induced electromotive force; optimizing the geometric design of the coils further based on at least one criterion for optimizing a further variation, due to a variation in distance between the testing head and the part to be inspected, of the induced electromotive force; optimizing geometric dimensions of each of the coils; and manufacturing the testing head in accordance with the geometric design of the coils carrying out the optimization.

10 Claims, 4 Drawing Sheets

(56) References Cited

U.S. PATENT DOCUMENTS

Figure 1:
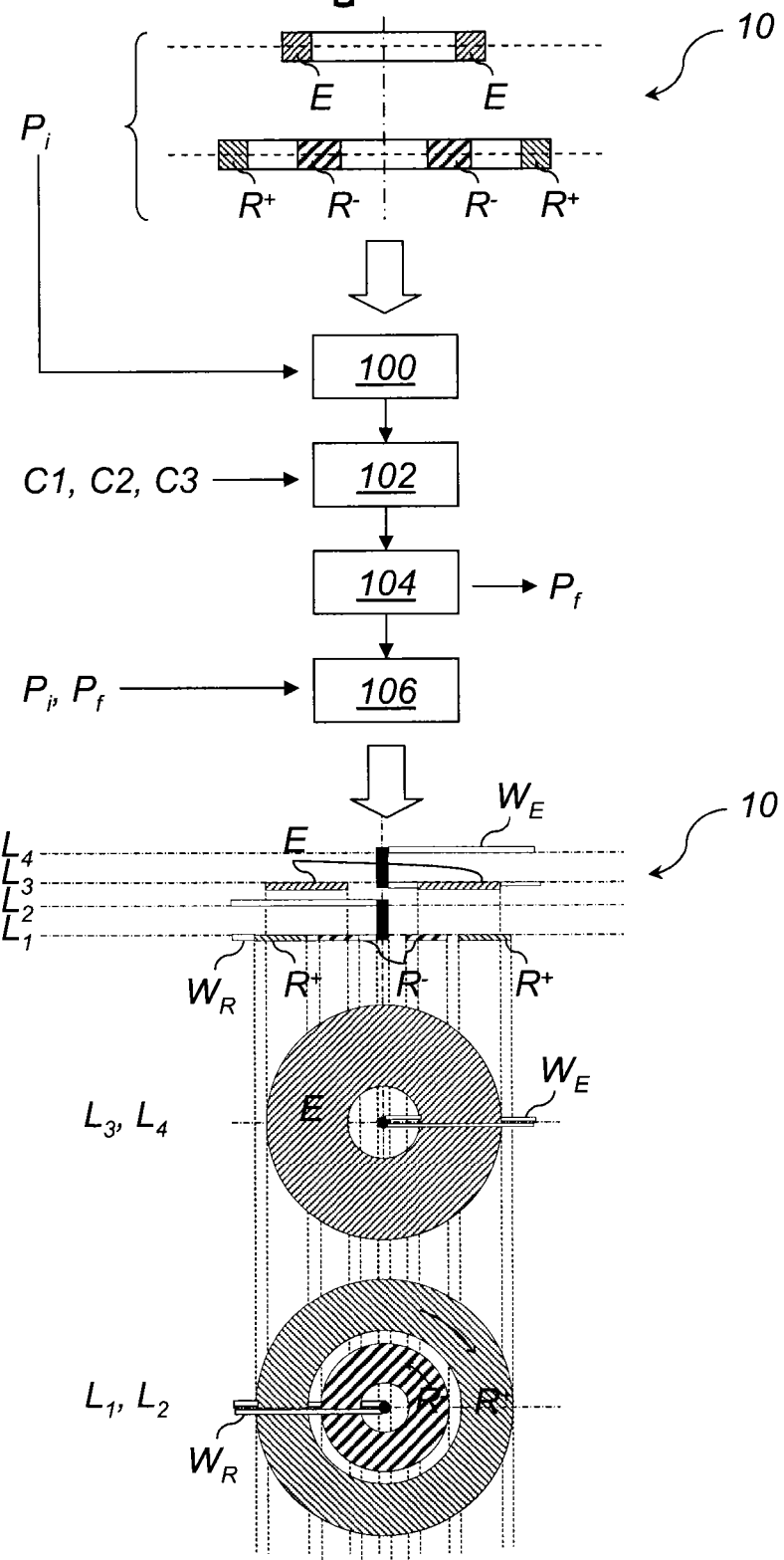

| | | | |
|---|---|---|---|
| 6,570,379 B2 * | 5/2003 | Crouzen | G01N 27/902 324/238 |
| 2009/0115411 A1 | 5/2009 | Sun et al. | |
| 2010/0134100 A1 | 6/2010 | Decitre | |
| 2010/0139081 A1 | 6/2010 | Decitre et al. | |

FOREIGN PATENT DOCUMENTS

| | | |
|---|---|---|
| FR | 2 881 827 | 8/2006 |
| FR | 2 904 693 | 2/2008 |
| FR | 2 904 694 | 2/2008 |

OTHER PUBLICATIONS

International Search Report Issued Mar. 7, 2013 in PCT/FR12/052797 Filed Dec. 4, 2012.

French Search Report Issued Jul. 17, 2012 in French Patent Application No. 1162342 Filed Dec. 22, 2011.

* cited by examiner

METHOD FOR MANUFACTURING A TESTING HEAD OF A NON-DESTRUCTIVE TESTING SENSOR BASED ON EDDY CURRENTS

The present invention relates to a method for manufacturing a testing head of a non-destructive testing sensor based on eddy currents.

A non-destructive testing sensor of this type uses the electromagnetic property of eddy currents for detecting defects such as cuts, cracks or corrosion in thin, not necessarily plane, conductive structures, such as aeronautical or nuclear metal parts. For example, this technology is suitable for inspecting steam generator tubes in nuclear power plants.

A testing head of such a sensor generally comprises at least one coil having a transmission function supplied with alternating current and at least one coil having a receiving function wherein an induced current flows, thus having an induced electromotive force having the same frequency as that of the alternating supply current. More specifically, when the testing head of the non-destructive testing sensor based on eddy currents is arranged in the vicinity of a part to be inspected, the coil having a transmission function is supplied with a sinusoidal signal. An electromagnetic field having the same frequency is then transmitted into the air and into the part to be inspected. This results, at the terminals of the coil having a receiving function, in an induced electromotive force from, on one hand, the coupling between the coil having a transmission function and the coil having a receiving function (this coupling being modified by the presence of the part) and, on the other, the magnetic field radiated by the currents induced in the part, conveying the potential presence of a defect therein.

In one embodiment having separate transmission and receiving functions, a testing head may comprise a first coil having a transmission function and a second coil having a receiving function. In differential receiving mode, a testing head according to this embodiment may comprise a first coil having a transmission function and two further coils having a receiving function mounted differentially. In differential transmission mode, a testing head according to this embodiment may comprise two coils having a transmission function mounted differentially and a third coil having a receiving function.

In a further embodiment having common transmission and receiving functions, a testing head may comprise a first coil having a simultaneous transmission and receiving function and a second coil having a simultaneous receiving and transmission function. In differential receiving or transmission mode, the two coils may be mounted differentially, for example in a Wheatstone bridge circuit.

In either of the embodiments mentioned above, a greater number of coils may be envisaged.

In any case, the geometric design of the coils may be optimized during the manufacture of a testing head based on some operating criteria. It is particularly advantageous to design a geometric coil design suitable for minimizing the electromotive force induced in the circuit having a receiving function when the testing head is at a predetermined nominal distance from a part to be inspected free from defects, this induced electromotive force being in this situation described as direct coupling. It is also advantageous to maximize any variation of the electromotive force induced in the circuit having a receiving function when this variation is due to the presence of a standard defect to be detected in the part to be inspected when the testing head is at the same predetermined nominal distance from the part. Indeed, this makes it possible to limit the amplification of the useful signal represented by the variation in electromotive force due to the presence of the defect and facilitate the detection thereof.

The invention thus applies more particularly to the manufacture of testing heads comprising at least two coils having transmission and/or receiving functions and relates to a manufacturing method comprising the following steps:
  optimizing a geometric design of the coils of the testing head based on at least one of the following criteria:
    minimizing an electromotive force E induced in at least one coil having a receiving function when the testing head is at a predetermined nominal distance from a part to be inspected free from defects, and
    maximizing a variation $\Delta e$ of said induced electromotive force E, this variation $\Delta e$ being due to the presence of a standard defect to be detected in the part to be inspected when the testing head is at said nominal distance from the part to be inspected,
  manufacturing the testing head in accordance with the geometric design of the coils carrying out this optimization.

Such a manufacturing method is for example disclosed in the French patent published under the number FR 2 881 827 B1. More specifically, in this document, a criterion for maximizing the modulus of the ratio $\Delta e/E$, when E and $\Delta e$ are expressed as complex values, is used to select an optimal distance between the respective axes of a transmission coil and a receiving coil. The useful signal indicating a defect then has the advantage of being monopolar and very fine, thus enabling correct location of the defect.

However, this method applies restrictively to an embodiment having separate transmission and receiving functions, in non-differential mode. Furthermore, it gives rise to a geometric design with overlapping of the two coils such that the testing head has a preferred detection axis. Consequently, the sensor is not isotropic, so much so that the useful signals indicating two defects of the same length but different orientations have amplitudes and shapes that may be considerably different. However, an identical shape (within one rotation) would be desirable, whether for detecting all the defects present in the part or for estimating geometric parameters of these defects.

Such a manufacturing method is also disclosed in an embodiment of the US patent published under the number U.S. Pat. No. 6,310,476 B1. According to this embodiment, the design of the coils is such that they are all coaxial, but the receiving function is performed by two coils mounted in differential mode. With an optimized size, this design makes it possible to design an isotropic sensor while minimizing direct coupling between the transmission and receiving functions.

On the other hand, it remains sensitive to air gap variations, i.e. variations in distance between the testing head and the part to be tested when the sensor is moved over same. However, air gap variations are inevitable in routine use of a non-destructive testing sensor, for example due to vibrations or, in the case of a part to be inspected having a complex shape, in that the sensor, even when flexible, cannot mold the part precisely. They are then liable to modify the coupling between the transmission and receiving functions of the sensor and thus create noise detrimental to defect detection.

This sensitivity to air gap variations may be enhanced, as proposed in further embodiments of the US patent published under the number U.S. Pat. No. 6,310,476 B1, but at the expense of a greater number of coils having a receiving function and thus a larger size. Moreover, in these further embodiments, the coaxiality of the coils is no longer verified.

A slightly different method is disclosed in the French patent published under the number FR 2 904 694 B1 where a distance between the transmission and receiving coils is optimized on the basis of a specific criterion for minimizing the sensitivity to air gap variations.

However, this method, as that described in the document FR 2 881 827 B1, applies restrictively to an embodiment having separate transmission and receiving functions, in non-differential mode. Moreover, it also gives rise to a geometric design having a preferred detection axis. Finally, it is incompatible with that described in the first embodiment of the document U.S. Pat. No. 6,310,476 B1.

It may thus be sought to provide a method for manufacturing a testing head of a non-destructive testing sensor based on eddy currents suitable for doing away with at least some of the problems and constraints mentioned above.

The invention thus relates to a method for manufacturing a testing head of a non-destructive testing sensor based on eddy currents, this testing head comprising at least two coils having transmission and/or receiving functions, comprising the following steps:
optimizing a geometric design of the coils of the testing head based on at least one of the following criteria:
minimizing an electromotive force E induced in at least one coil having a receiving function when the testing head is at a predetermined nominal distance from a part to be inspected free from defects, and
maximizing a variation $\Delta e$ of said induced electromotive force E, this variation $\Delta e$ being due to the presence of a standard defect to be detected in the part to be inspected when the testing head is at said nominal distance from the part to be inspected,
manufacturing the testing head in accordance with the geometric design of the coils carrying out this optimization,
wherein:
the optimization of the geometric design of the coils is further carried out based on at least one criterion for optimizing a further variation $\Delta E$ of said induced electromotive force E, this further variation $\Delta E$ being due to a variation in distance between the testing head and the part to be inspected, and
the optimization of the geometric design of the coils comprises optimization of geometric dimensions of each of these coils.

In this way, the optimization of the geometric design of the coils may be carried out based on a plurality of geometric design parameters of the coils of the testing head and according to a plurality of criteria including at least one of the quantities E or $\Delta e$ and the quantity $\Delta E$. It is thus possible, with great flexibility in the optimization criteria and in the parameters to be optimized, to manufacture a testing head having a high sensitivity to defects, a low sensitivity to the noise generated by air gap variations and a satisfactory dynamic detection range.

Optionally, the geometric design of the coils of the testing head is previously set by imposing at least one of the elements of the set consisting of a number of coils, an allocation in respect of transmission and/or receiving function for each coil and the coaxiality of all the coils.

In particular, if coaxiality of the coils is applied, an isotropic sensor may be designed.

Also optionally, the geometric design of the coils of the testing head is optimized by varying at least one of the elements of the set consisting of the internal and external diameters of each coil, the number of turns thereof, the thickness thereof, the nominal distance relative to the part to be inspected and the electrical frequency of the currents flowing in the coils.

Also optionally, the optimization of the geometric design of the coils of the testing head is carried out inter alia based on a criterion for minimizing the ratio $|E|/|\Delta e|$, where $|E|$ and $|\Delta e|$ are the respective moduli of E and $\Delta e$ expressed in complex form.

Also optionally, the optimization of the geometric design of the coils of the testing head is carried out inter alia based on a criterion for minimizing the ratio $|\Delta E|/|\Delta e|$, where $|\Delta E|$ and $|\Delta e|$ are the respective moduli of $\Delta E$ and $\Delta e$ expressed in complex form.

Also optionally, the optimization of the geometric design of the coils of the testing head is carried out inter alia based on a criterion for minimizing the difference between, on one hand, $+/-\pi/2$ and, on the other, the phase shift between $\Delta E$ and $\Delta e$ expressed in complex form.

Also optionally, the optimization of the geometric design of the coils of the testing head is carried out inter alia based on a criterion for minimizing the ratio:

$$\frac{\cos[\varphi(\Delta E) - \varphi(\Delta e)]}{|\Delta e|},$$

or in an equivalent manner the ratio:

$$\frac{\cotan[\varphi(\Delta E) - \varphi(\Delta e)]}{|\Delta e|},$$

where $\phi(\Delta E)$ and $\phi(\Delta e)$ are the respective phases of $\Delta E$ and $\Delta e$ expressed in complex form, $|\Delta e|$ being the modulus of $\Delta e$.

Also optionally, the optimization is carried out on the basis of:
a simulation of the geometric design of the coils of the testing head suitable for evaluating said induced electromotive force E, said variation $\Delta e$ and said further variation $\Delta E$, and
a non-linear and non-constrained Nelder-Mead type multidimensional optimization, particularly a minimization, applied to said criteria.

Also optionally, the geometric design of the coils of the testing head is previously set by applying the following constraints:
the number of coils of the testing head is set to three, including one transmission coil and two receiving coils mounted in differential mode,
the three coils of the testing head are annular and coaxial,
the two receiving coils of the testing head are further coplanar.

Also optionally, the geometric design of the coils of the testing head is previously set by applying the following constraints:
the number of coils of the testing head is set to two, each having a common transmission/receiving function,
these two coils are mounted in differential mode in a Wheatstone bridge circuit,
these two coils are annular, coplanar and coaxial.

Figure 2:
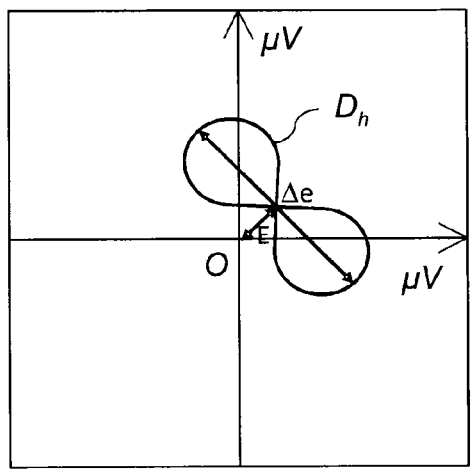
Figure 3:
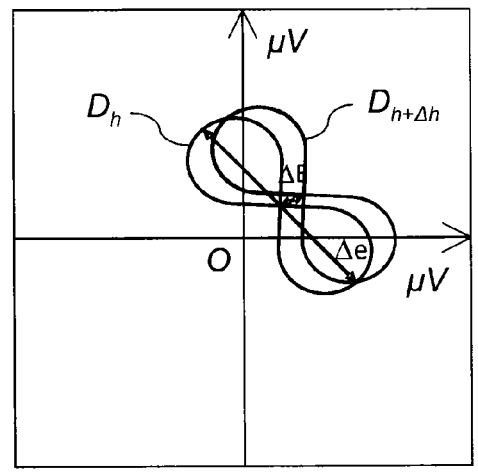
Figure 4:
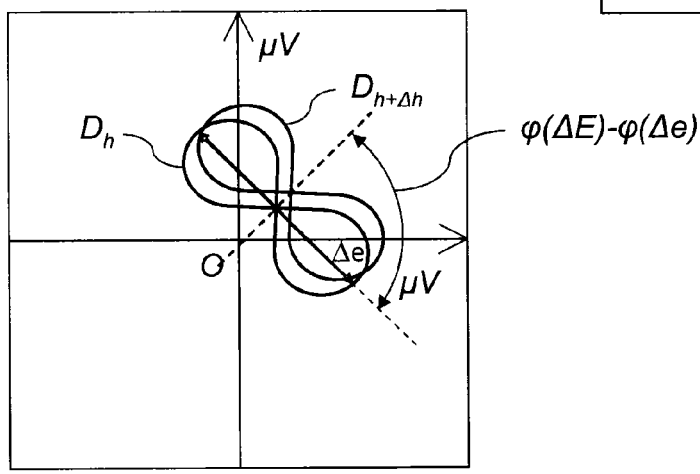
Figure 5:
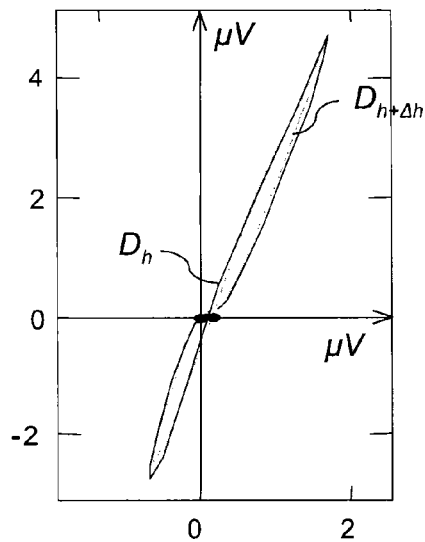
Figure 6:
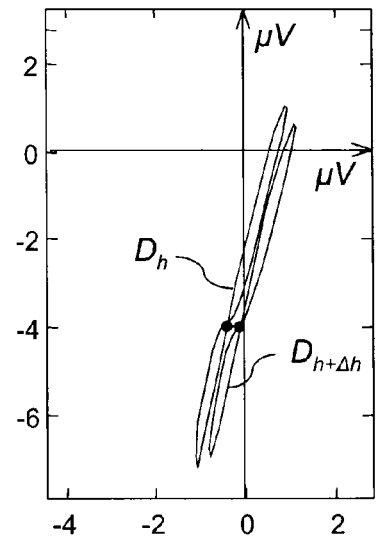
Figure 7:
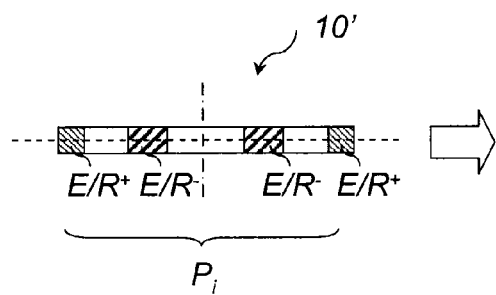
Figure 7:
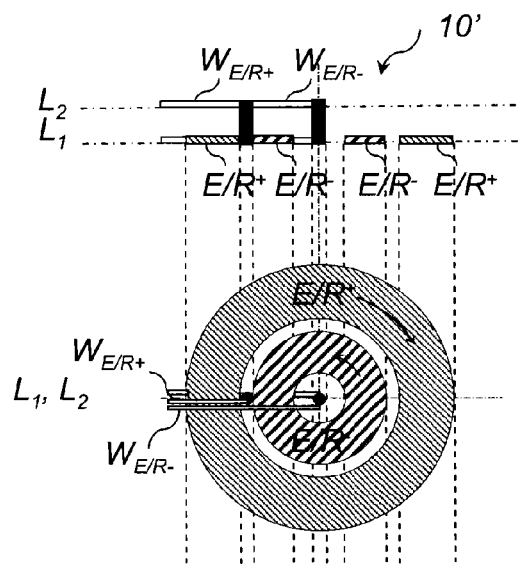
Figure 8:
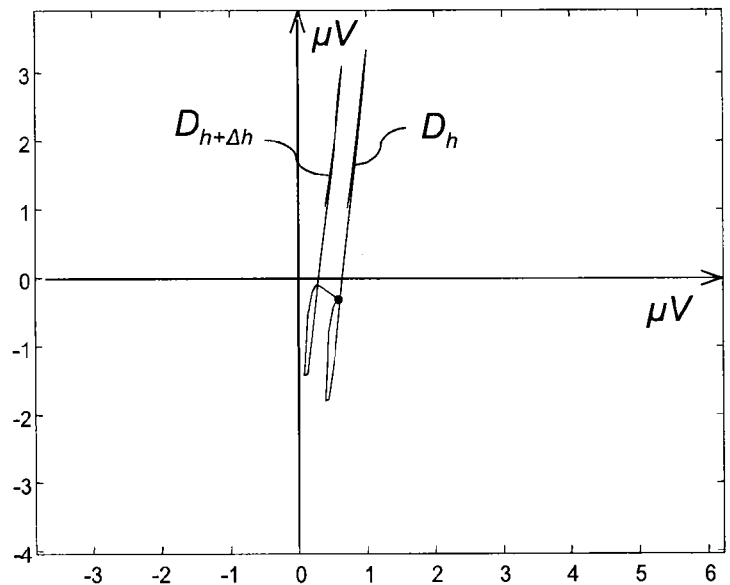
Figure 9:
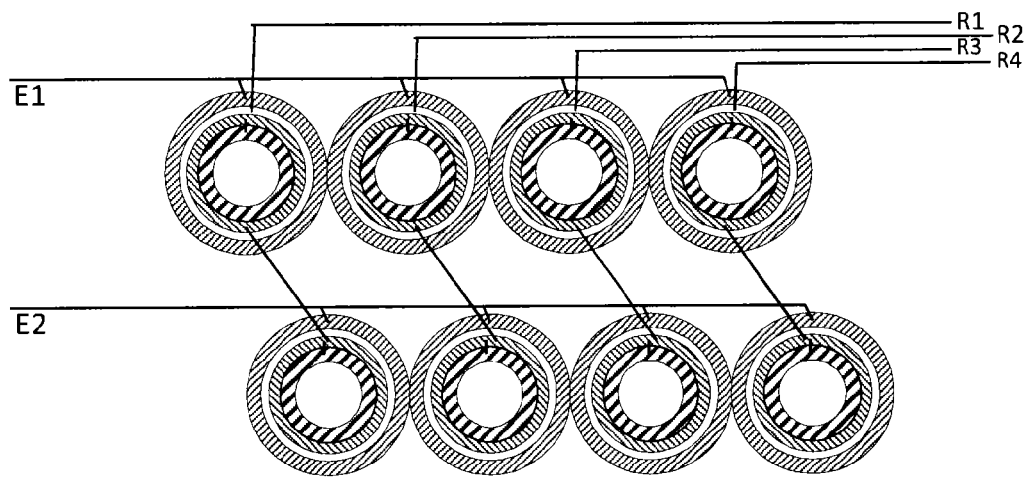

The invention will be understood more clearly using the following description, given merely as an example, with reference to the appended figures wherein:

FIG. 1 illustrates the successive steps of a method for manufacturing a testing head of a non-destructive testing sensor based on eddy currents, according to one embodiment of the invention, FIGS. 2, 3 and 4 are diagrams illustrating, in a complex plane, optimization criteria used in the manufacturing method in FIG. 1, FIGS. 5 and 6 are diagrams illustrating, in a complex plane, optimization results obtained by implementing the manufacturing method in FIG. 1, for a testing head design having separate transmission and receiving functions in differential receiving mode, FIG. 7 illustrates the result of the implementation of the manufacturing method in FIG. 1, based on a testing head design having a common transmission/receiving function of the coils thereof and in differential receiving mode, FIG. 8 is a diagram illustrating, in a complex plane, an optimization result obtained by implementing the manufacturing method in FIG. 1, for the testing head design in FIG. 7, and FIG. 9 illustrates schematically the design principle, by means of the implementation of the manufacturing method in FIG. 1, of a matrix multi-element testing head.

Merely as an illustration, the manufacturing method in FIG. 1 is described for the particular design of a testing head 10 having three coaxial coils, including one coil having a transmission function and two coils having a receiving function mounted in differential mode. However, as can be seen hereinafter, this method may apply to further testing head designs.

During a first initialization step 100, some parameters $P_i$ of the geometric design of the coils of the testing head 10 are set. In the example in FIG. 1 mentioned above:
 the number of coils of the sought testing head 10 is set to three, including one transmission coil E and two receiving coils $R^+$ and $R^-$ mounted in differential mode,
 the three coils E, $R^+$ and $R^-$ are annular and coaxial,
 the two receiving coils $R^+$ and $R^-$ are further coplanar.

As a general rule, the geometric design of the coils of the testing head 10 is previously set during this step by imposing a number of coils, an allocation in respect of the transmission and/or receiving function for each coil, coaxiality of at least some of the coils or further constraining parameters according to the target application or the sought scenario. In this way, a large number of testing head designs may be envisaged.

Then, during an optimization step 102, based on the parameters $P_i$ set in the initialization step 100, further so-called final parameters $P_f$ enabling concrete manufacture of the testing head 10, are set and modified within the scope of a multidimensional optimization and having multiple criteria in respect of the geometric design of the coils of the testing head 10.

These final parameters $P_f$ particularly comprise at least the geometric dimension parameters of each of the coils defined in the initialization step 100. Therefore, they comprise, for example, when the coils are annular, the values of the internal and external diameters of each coil and the values of the respective thicknesses thereof. The final parameters may further comprise the number of turns in each coil, or the value of the nominal distance between the testing head 10 and the part to be inspected, when a protective insulating layer is to be provided between the coils of the testing head and the surface of the part to be inspected against which this protective and insulating layer is intended to be placed in contact. They may also comprise the value of the electrical frequency of the currents flowing in the coils, although this may alternatively be set at initialization 100.

Some of the final parameters are interrelated. For example, given that an overlap of the receiving coils $R^+$ and $R^-$ is not permitted in view of the parameters set at initialization 100 (they are coplanar), the smaller external diameter of these two coils is necessarily less than the internal diameter of the other. Further parameters have a limited variation range, such as the numbers of turns.

In the example in FIG. 1, the criteria based on which the multidimensional optimization of the geometric design of the coils is carried out comprise a first criterion referenced C1 for:
 minimizing an electromotive force E induced at the terminals of the circuit consisting of the two receiving coils $R^+$ and $R^-$ when the testing head 10 is at a predetermined nominal distance h from a part to be inspected free from defects, and/or
 maximizing a variation $\Delta e$ of said induced electromotive force E, this variation $\Delta e$ being due to the presence of a standard defect to be detected in the part to be inspected when the testing head is at the nominal distance h.

The criterion C1 may then be described as the criterion for minimizing the direct coupling E (including the effect of the closeness of a part to be inspected free from defects) between the transmission and receiving functions of the testing head 10, in the light of the measurement $\Delta e$ to be made by the testing head 10 to detect any defects.

By way of example, the criterion C1 may be more specifically defined so as to maximize the variation $\Delta e$ due to the presence of a defect in relation to the direct coupling E, which may particularly be expressed using the ratio $|E|/|\Delta e|$ to be minimized, where $|E|$ and $|\Delta e|$ are the respective moduli of E and $\Delta e$ when these quantities are expressed in complex form. Alternatively, the criterion C1 may adopt other forms than the ratio expressed above, a plurality of equivalent forms being suitable for being envisaged to maximize $\Delta e$ in relation to E.

An illustration of the optimization of the criterion C1 is given by FIG. 2 wherein a diagram represents, in the complex plane, the variations of the induced electromotive force $E+\Delta e$ at the terminals of the receiving circuit of the testing head 10 in the presence of a standard defect in the part to be inspected. The characteristic signal of the standard defect to be detected is the closed curve $D_h$ in the shape of an "8". The largest dimension thereof gives the maximum range of the variation of the induced electromotive force due to the presence of the standard defect. This maximum range may be adopted as the value of $|\Delta e|$. The distance between the center of the curve $D_h$ (no defect detected) and the center O of the complex plane gives the value of $|E|$. Optimizing the criterion C1 thus consists of obtaining the largest possible curve $D_h$ and as close as possible to the origin O in the complex plane.

In the example in FIG. 1, the criteria based on which the multidimensional optimization of the geometric design of the coils is carried out further comprise a second criterion referenced C2 for optimizing a further variation $\Delta E$ of said induced electromotive force E, this further variation $\Delta E$ being due to a variation of the distance between the testing head 10 and the part to be inspected, for example when the testing head 10 is moved relative to the part.

The criterion C2 may then be described as a criterion for minimizing the sensitivity of the testing head 10 to air gap variations. It may further be expressed relative to the measurement $\Delta e$ to be made by the testing head 10 to detect any defects.

By way of example, the criterion C2 may be more specifically defined so as to maximize the variation $\Delta e$ due to the presence of a defect relative to the variation $\Delta E$ due to air gap variations, which may particularly be expressed using the ratio $|\Delta E|/|\Delta e|$ to be minimized, where $|\Delta E|$ and $|\Delta e|$ are the respective moduli of $\Delta E$ and $\Delta e$ when these quantities are expressed in complex form. Alternatively, the criterion C2 may adopt other forms than the ratio expressed above, a plurality of equivalent forms being suitable for being envisaged to maximize Δe in relation to ΔE.

An illustration of the optimization of the criterion C2 is given by FIG. 3 wherein a diagram represents, in the complex plane, variations of the induced electromotive force E+Δe at the terminals of the receiving circuit of the testing head 10 in the presence of a standard defect in the part to be inspected, for two distance values between the testing head 10 and the part to be inspected, for example said nominal distance h and a further distance h+Δh. In this way, two closed curves in the shape of an "8" approximately of the same size but offset in relation to each other are obtained. The first is the curve $D_h$ in FIG. 2, the second is a curve $D_{h+\Delta h}$ corresponding to the distance h+Δh. The distance between the center of the curve $D_h$ and that of the curve $D_{h+\Delta h}$ gives the value of |ΔE|, whereas that of |Δe| is always given by the largest dimension of the curve $D_h$ (or $D_{h+\Delta h}$). Optimizing the criterion C2 thus consists of obtaining that the curves $D_h$ and $D_{h+\Delta h}$ are as close as possible to each other in the complex plane.

In the example in FIG. 1, the criteria based on which the multidimensional optimization of the geometric design of the coils is carried out further comprise a third criterion referenced C3 for optimizing the variation ΔE.

The criterion C3 may then be described, like the criterion C2, as a criterion for minimizing the sensitivity of the testing head 10 to air gap variations. It may further also be expressed relative to the measurement Δe to be made by the testing head 10 to detect any defects.

By way of example, the criterion C3 may be more specifically defined so as to optimize the phase shift between the variation Δe due to the presence of a defect and the variation ΔE due to air gap variations, so as to render these two variations readily discriminable. In particular, it is sought for this phase shift to be as close as possible to a right angle, i.e. +/−π/2. The criterion C3 may thus particularly be expressed using the following ratio to be minimized:

$$\frac{\cos[\varphi(\Delta E) - \varphi(\Delta e)]}{|\Delta e|},$$

or in an equivalent manner, $$\frac{\cotan[\varphi(\Delta E) - \varphi(\Delta e)]}{|\Delta e|},$$

where φ(ΔE) and φ(Δe) are the respective phases of ΔE and Δe expressed in complex form, |Δe| still being the modulus of Δe. Alternatively, the criterion C3 may adopt other forms than the two ratios expressed above, a plurality of equivalent forms being suitable for being envisaged to optimize the phase shift between Δe and ΔE.

An illustration of the optimization of the criterion C3 is given by FIG. 4 wherein a diagram represents, in the complex plane, the same curves $D_h$ and $D_{h+\Delta h}$ as in FIG. 3. However, in FIG. 4, to account for the criterion C3, the phase shift φ(ΔE)−φ(Δe) between Δe and ΔE is the relevant value to be optimized by approximately a right angle as closely as possible. Optimizing the criterion C3 thus consists of obtaining that the shift between the curves $D_h$ and $D_{h+\Delta h}$ is as orthogonal as possible to the vector Δe, the latter having a modulus that is as large as possible.

In the example in FIG. 1, the three criteria C1, C2 and C3 are used during the optimization step 102. However, alternatively, while remaining within the scope of the invention, only the criteria C1 and C2, or C1 and C3, may be taken into account.

The optimization step 102, which is multidimensional (due to the presence of a plurality of final parameters $P_f$ to be optimized), in principle non-linear, non-constrained and based on multiple criteria (due to the inclusion of C1 and C2, or C1 and C3, or C1 and C2 and C3), may be executed using various known algorithms. In practical terms, by expressing this optimization in the form of a multidimensional, non-linear and non-constrained function to be minimized, the Nelder-Mead algorithm may be used at this stage of the manufacturing method. Alternatively, genetic algorithms less sensitive to local minima may also be used.

During this optimization of the final parameters $P_f$ to meet the adopted criteria, the geometric design of the coils is advantageously simulated to evaluate the direct coupling E, said variation Δe and said further variation ΔE. The simulation is performed for example using the non-destructive testing simulation software known as CIVA (registered trademark), or any other simulation software particularly using finite elements.

The optimization step 102 is followed by a step 104 for selecting the final parameters $P_f$ carrying out this optimization.

Finally, during a final step 106, the testing head 10 is manufactured in accordance with the geometric design of the coils defined by the initial $P_i$ and final $P_f$ parameters.

As illustrated in the bottom section of FIG. 1, in sectional and top views, the testing head 10 obtained following the manufacturing step 106 is embodied in concrete terms on a 50 μm thick flexible polyimide film having four layers $L_1$, $L_2$, $L_3$ and $L_4$. The thickness of the three coils E, $R^+$ and $R^-$ is for example equal to the thickness of a copper track, i.e. for this example 9 μm. For the coil having a transmission function E, the transmission circuit wherein it is integrated and the turns thereof are represented by a copper wire $W_E$. For the two coils having a receiving function $R^+$ and $R^-$, the receiving circuit wherein they are mounted in differential mode along with the turns thereof are represented by a copper wire $W_R$.

On the bottom layer $L_1$, the copper wire $W_R$ winds in a first direction from the external diameter of the coil $R^+$ to the internal diameter thereof, thus forming the coil $R^+$, and then winds in a second direction opposite the first from the external diameter of the coil $R^-$ to the internal diameter thereof, thus forming the coil $R^-$. It then moves up along the common axis of the two coils $R^+$ and $R^-$ towards the layer $L_2$, by means of a via. This layer $L_2$ merely fulfils a routing function of the copper wire $W_R$ for the formation of the receiving circuit. On the layer $L_3$, the copper wire $W_E$ winds in a predetermined direction from the external diameter of the coil E to the internal diameter thereof, thus forming the coil E. It then moves up along the axis of the coil E, which is also common to the two coils $R^+$ and $R^-$, towards the top layer $L_4$, by means of a via. This top layer $L_4$ merely fulfils a routing function of the copper wire $W_E$ for the formation of the transmission circuit.

In an experimental context, the following constraints were further added:
  the number of turns of the three coils should be maximal to increase the sensitivity and, for technological reasons, the resolution of the turns is set to 160 μm (width of copper track+width of insulator between turns),
  the internal and external diameters of the coils are adjusted to obtain an integer number of turns, a 50 µm thick polyimide self-adhesive tape is used to protect the face of the testing head 10 in contact with the part to be inspected, the standard defect to be detected in the part is as follows: surface defect of 1 mm in length, 100 µm in aperture and 500 µm in depth, the air gap variation Δh taken into account in the optimization step 102 is 25 µm during the movement of the testing head 10, the electrical frequency of the currents flowing in the coils is initially set to 1 MHz, this parameter also being adjusted during the optimization step 102.

According to a weighting of the three criteria C1, C2 and C3 in favor of the first two, the following geometric design is obtained for example in the step 104:

Transmission coil E: internal diameter=0.3880 mm,
 external diameter=6.3080 mm,
 number of turns=19.
Receiving coil R⁻: internal diameter=1.4240 mm,
 external diameter=3.5040 mm,
 number of turns=7.
Receiving coil R⁺: internal diameter=4.3640 mm,
 external diameter=5.4840 mm,
 number of turns=4.
Optimized electrical frequency: very close to 1 MHz.

For this design, FIG. 5 illustrates, using an equivalent diagram to that in FIG. 3 or 4, the curves $D_h$ and $D_{h+\Delta h}$, where h=50 µm and Δh=25 µm.

It is noted that:

in the absence of a defect (center of the curve $D_h$), the signal detected is very close to the origin O of the complex plane, thus the direct coupling E is practically zero, furthermore, the direct coupling E is very small relative to the variation Δe due to the presence of the standard defect (criterion C1 met), for an air gap variation Δh, the variation ΔE due to this air gap variation is very small relative to the variation Δe due to the presence of the standard defect (criterion C2 met), and the phase difference between ΔE and Δe is close to 5π/12 (criterion C3 met to a lesser degree).

According to a further weighting of the three criteria C1, C2 and C3 in favor of the third, the following geometric design is obtained for example in the step 104:

Transmission coil E: internal diameter=0.3780 mm,
 external diameter=6.2980 mm,
 number of turns=19.
Receiving coil R⁻: internal diameter=1.5180 mm,
 external diameter=3.9180 mm,
 number of turns=8.
Receiving coil R⁺: internal diameter=4.1300 mm,
 external diameter=5.5700 mm,
 number of turns=4.
Optimized electrical frequency: very close to 1 MHz.

For this design, FIG. 6 illustrates, using an equivalent diagram to that in FIG. 3 or 4, the curves $D_h$ and $D_{h+\Delta h}$, where h=50 µm and Δh=25 µm.

It is noted that the phase difference between ΔE and Δe is close to π/2 (criterion C3 met), in exchange for less optimal values of E and ΔE (criteria C1 and C2 met to a lesser degree).

The manufacturing method in FIG. 1 has been described for the design of a testing head 10 having three coaxial coils, including one coil having a transmission function and two coils having a receiving function mounted in differential mode. However, it also applies for example for the design of a testing head 10' having two coaxial coils, both having a common transmission and receiving function, receiving being performed in differential mode. This is the subject matter of FIG. 7 schematically illustrating such a design of a testing head 10'.

During a first initialization step 100, some parameters $P_i$ of the geometric design of the coils of the testing head 10' are set. In the example in FIG. 7:

the number of coils of the sought testing head 10' is set to two, including one coil having a common transmission/receiving function referenced E/R⁺ and a further coil having a common transmission/receiving function referenced E/R⁻, these two coils are mounted in differential mode in a Wheatstone bridge circuit, the two coils E/R⁺ et E/R⁻ are annular, coplanar and coaxial.

As illustrated in the right section of FIG. 7, in sectional and top views, the testing head 10' obtained following the manufacturing step 106 is embodied in concrete terms on a flexible polyimide film having two layers $L_1$ and $L_2$. The thickness of the two coils E/R⁺ and E/R⁻ is for example equal to the thickness of a copper track, i.e. for this example 9 µm. For the coil E/R⁺, the circuit wherein it is integrated and the turns thereof are represented by a copper wire $W_{E/R+}$. For the coil E/R⁻, the circuit wherein it is integrated and the turns thereof are represented by a copper wire $W_{E/R-}$.

On the bottom layer $L_1$, the copper wire $W_R$ winds in a first direction from the external diameter of the coil E/R⁺ to the internal diameter thereof, thus forming the coil E/R⁺. It then moves up in a gap reserved between the two coils towards the top layer $L_2$, by means of a via. Similarly, on the bottom layer $L_1$, the copper wire $W_{E/R-}$ winds in a second direction opposite the first from the external diameter of the coil E/R⁻ to the internal diameter thereof, thus forming the coil E/R⁻. It then moves up along the common axis of the two coils E/R⁺ and E/R⁻ towards the top layer $L_2$, by means of a via. The top layer $L_2$ merely fulfils a routing function of the copper wires $W_{E/R+}$ and $W_{E/R-}$.

According to one possible weighting of the three criteria C1, C2 and C3, the following geometric design is obtained for example in the step 104:

Transmission/receiving coil E/R⁻: internal diameter=0.36 mm,
 external diameter=2.44 mm,
 number of turns=7.
Transmission/receiving coil E/R⁺: internal diameter=2.68 mm,
 external diameter=3.80 mm,
 number of turns=4.
Optimized electrical frequency: very close to 1 MHz.

For this design, FIG. 8 illustrates, using an equivalent diagram to that in FIG. 3 or 4, the curves $D_h$ and $D_{h+\Delta h}$, where h=50 µm and Δh=25 µm.

It is noted that:

in the absence of a defect (center of the curve $D_h$), the signal detected is relatively close to the origin O of the complex plane, thus the direct coupling E is relatively low, furthermore, the direct coupling E is relatively small relative to the variation Δe due to the presence of the standard defect (criterion C1 more or less met), for an air gap variation Δh, the variation ΔE due to this air gap variation is relatively small relative to the variation Δe due to the presence of the standard defect (criterion C2 more or less met), and the phase difference between ΔE and Δe is close to π/2 (criterion C3 met satisfactorily).

As a general rule, the manufacturing method in FIG. 1 applies for the design of testing heads having very diverse geometric designs:

- configurations having one transmission coil and two receiving coils in differential mode, as seen with reference to FIG. 1, but wherein the coils may be ordered in different ways on the substrate layers, optionally coplanar, different thicknesses, etc.,
- configurations having two transmission coils in differential mode and one receiving coil, but wherein the coils may also be ordered in different ways on the substrate layers, optionally coplanar, different thicknesses, etc.,
- configurations having two coils having a common transmission/receiving function, as seen with reference to FIG. 7, but wherein the coils may be ordered in different ways on the substrate layers, optionally coplanar, different thicknesses, etc.,
- configurations having a number of coils greater than three.

Also as a general rule, the manufacturing method described above is suitable for testing heads wherein the coils of varied types such as wired, printed or etched on flexible or rigid substrates.

A coaxial ferrite core may also be arranged on one or a plurality of the coils of the testing head or even cover all the coils.

Moreover, as illustrated in FIG. 9, the basic pattern, illustrated in FIGS. 1 and 8 and obtained by implementing the manufacturing method described above, may be repeated for the manufacture of a multi-element testing head. Furthermore, in an embodiment having separate transmission and receiving functions as is the case of the example in FIG. 1, a matrix arrangement with connection of the elements in rows (E1, E2) and in columns (R1, R2, R3, R4) is possible according to the same method as that used and described in the French patent published under the number FR 2 904 693 B1. It may then be envisaged to offer a version of a sensor comprising such a testing head in the form of a static two-dimensional imager, the coaxiality of the coils further making it possible to reduce the gray areas (i.e. areas wherein defects cannot be detected).

In sum, it is obvious that a manufacturing method such as that described above is suitable for designing testing heads of non-destructive testing sensors based on eddy currents having the following advantages:

- high sensitivity to defects present in the part to be inspected,
- low sensitivity to air gap variation noise,
- isotropism,
- large dynamic range, thus having low direct coupling, to enable satisfactory amplification of signals indicating defects,
- optimal phase shift between electromotive force variations due to air gap variations and those due to defects,
- performance of geometric design (coaxiality) for defect detection,
- ready production on flexible polyimide film, in at least three layers for testing heads having separate transmission and receiving functions, or at least two layers for testing heads having a common transmission/receiving function,
- option of simple matrix connection for the embodiment of imagers with one connection mode of the transmission coils per row and the receiving coils, the image then being obtained by movement along a sensor axis,
- due to the compact size of the geometric design of the basic pattern, option to design static two-dimensional type sensors minimizing gray areas, suitable for being made from flexible polyimide film with multiple layers.

It should be noted that the invention is not limited to the embodiments described above. It will be obvious to those skilled in the art that various modifications may be made to the embodiments described above, in the light of the teaching disclosed herein. In the claims hereinafter, the terms used should not be interpreted as limiting the claims to the embodiments disclosed in the present description, but should be interpreted to include any equivalents intended to be covered by the claims due to the wording thereof and which can be envisaged by those skilled in the art by applying their general knowledge to the implementation of the teaching disclosed herein.

The invention claimed is:

1. A method for manufacturing a testing head of a non-destructive testing sensor based on eddy currents, the testing head including at least two coils having transmission and/or receiving functions, the method comprising:
   optimizing a geometric design of the coils of the testing head based on at least one of following criteria:
     minimizing an electromotive force E induced in at least one coil having a receiving function when the testing head is at a predetermined nominal distance from a part to be inspected free from defects, and
     maximizing a variation $\Delta e$ of the induced electromotive force E, the variation $\Delta e$ being due to presence of a standard defect to be detected in the part to be inspected when the testing head is at the nominal distance from the part to be inspected;
   optimizing the geometric design of the coils further based on at least one criterion for optimizing a further variation $\Delta E$ of the induced electromotive force E, the further variation $\Delta E$ being due to a variation in distance between the testing head and the part to be inspected;
   optimizing geometric dimensions of each of the coils; and
   manufacturing testing head in accordance with the geometric design of the coils carrying out the optimizings.

2. The method for manufacturing a testing head as claimed in claim 1, wherein the geometric design of the coils of the testing head is previously set by imposing at least one of the elements of a set of a number of coils, an allocation in respect of transmission and/or receiving function for each coil, and coaxiality of all the coils.

3. The method for manufacturing a testing head as claimed in claim 1, wherein the geometric design of the coils of the testing head optimized by varying at least one of elements of a set of internal and external diameters of each coil, a number of turns thereof, a thickness thereof, a nominal distance relative to the part to be inspected, and electrical frequency of currents flowing in the coils.

4. The method for manufacturing a testing head as claimed in claim 1, wherein the optimizing the geometric design of the coils of the testing head is carried out inter alia based on a criterion for minimizing ratio $|E|/|\Delta e|$, where $|E|$ and $|\Delta e|$ are the respective moduli of E and $\Delta e$ expressed in complex form.

5. The method for manufacturing a testing head as claimed in claim 1, wherein the optimizing the geometric design of the coils of the testing head is carried out inter alia based on a criterion for minimizing ratio $|\Delta E|/|\Delta e|$, where $|\Delta E|$ and $|\Delta e|$ are the respective moduli of $\Delta E$ and $\Delta e$ expressed in complex form.

6. The method for manufacturing a testing head as claimed in claim 1, wherein the optimizing the geometric design of the coils of the testing head is carried out inter alia based on a criterion for minimizing the difference between $+/-\pi/2$ and a phase shift between $\Delta E$ and $\Delta e$ expressed in complex form.

7. The method for manufacturing a testing head as claimed in claim 1, wherein the optimizing the geometric design of the coils of the testing head is carried out inter alia based on a criterion for minimizing ratio:

$$\frac{\cos[\varphi(\Delta E) - \varphi(\Delta e)]}{|\Delta e|},$$

or in an equivalent manner ratio:

$$\frac{\cotan[\varphi(\Delta E) - \varphi(\Delta e)]}{|\Delta e|},$$

where $\phi(\Delta E)$ and $\phi(\Delta e)$ are the respective phases of $\Delta E$ and $\Delta e$ expressed in complex form, $|\Delta e|$ being the modulus of $\Delta e$.

8. The method for manufacturing a testing head as claimed in claim 1, wherein the optimizing is carried out on the basis of:
- a simulation of the geometric design of the coils of the testing head suitable for evaluating the induced electromotive force E, the variation $\Delta e$, and the further variation $\Delta E$, and
- a non-linear and non-constrained Nelder-Mead type multidimensional optimization, or a minimization, applied to the criteria.

9. The method for manufacturing a testing head as claimed in claim 1, wherein the geometric design of the coils of the testing head is previously set by applying following constraints:
- a number of coils of the testing head is set to three, including one transmission coil and two receiving coils mounted in differential mode,
- the three coils of the testing head are annular and coaxial,
- the two receiving coils of the testing head are further coplanar.

10. The method for manufacturing a testing head as claimed in claim 1, wherein the geometric design of the coils of the testing head is previously set by applying following constraints:
- a number of coils of the testing head is set to two, each having a common transmission/receiving function,
- the two coils are mounted in differential mode in a Wheatstone bridge circuit,
- these two coils are annular, coplanar, and coaxial.

* * * * *